(12) United States Patent
Haas et al.

(10) Patent No.: US 7,364,718 B2
(45) Date of Patent: Apr. 29, 2008

(54) PROCESS FOR THE PRODUCTION OF HYDROGEN PEROXIDE

(75) Inventors: Thomas Haas, Frankfurt (DE); Robert Jahn, Rodenbach (DE)

(73) Assignee: Degussa AG, Düsseldorf (DE)

( * ) Notice: Subject to any disclaimer, the term of this patent is extended or adjusted under 35 U.S.C. 154(b) by 122 days.

(21) Appl. No.: 11/401,352

(22) Filed: Apr. 11, 2006

(65) Prior Publication Data

US 2006/0252947 A1    Nov. 9, 2006

Related U.S. Application Data

(60) Provisional application No. 60/670,229, filed on Apr. 12, 2005.

(30) Foreign Application Priority Data

Apr. 13, 2005    (DE)    ...................... 10 2005 016 877

(51) Int. Cl.
*C01B 15/029*    (2006.01)
*C01B 15/01*    (2006.01)
*C07D 301/12*    (2006.01)

(52) U.S. Cl. .................. 423/584; 252/186.29; 549/531

(58) Field of Classification Search .................. 423/584
See application file for complete search history.

(56) References Cited

U.S. PATENT DOCUMENTS

| 2,120,430 A | * | 6/1938 | Rieche ........................ 424/616 |
| 4,335,092 A | * | 6/1982 | Dalton et al. ................ 423/584 |
| 4,833,260 A | | 5/1989 | Neri |
| 5,236,692 A | | 8/1993 | Nagashima |
| 6,143,688 A | | 11/2000 | Thompson |
| 6,168,775 B1 | | 1/2001 | Zhou |
| 6,210,651 B1 | * | 4/2001 | Nystrom et al. ............ 423/584 |
| 6,245,157 B1 | | 6/2001 | Gerlach |
| 6,387,346 B1 | | 5/2002 | Bertsch-Frank |
| 7,241,908 B2 | | 7/2007 | Haas |
| 2003/0083510 A1 | | 5/2003 | Haas |
| 2003/0215383 A1 | | 11/2003 | Escrig |
| 2004/0151658 A1 | * | 8/2004 | Escrig et al. ................ 423/584 |
| 2005/0025697 A1 | * | 2/2005 | Rueter et al. ................ 423/584 |
| 2005/0063896 A1 | | 3/2005 | Jaeger |
| 2005/0069483 A1 | | 3/2005 | Goor |
| 2005/0276744 A1 | | 12/2005 | Haas |

FOREIGN PATENT DOCUMENTS

WO    WO 02/085873 A1    10/2002
WO    WO 2005/009611    2/2005

* cited by examiner

*Primary Examiner*—Wayne A. Langel
(74) *Attorney, Agent, or Firm*—Michael A. Sanzo; Law Office of Michael A. Sanzo, LLC

(57) ABSTRACT

Hydrogen peroxide is produced by reacting hydrogen and oxygen in the presence of a noble metal catalyst in a liquid reaction medium, the reaction being performed in the presence of a sulfuric acid alkyl ester. In the presence of sulfuric acid alkyl esters the noble metal catalyst exhibits a high and lasting activity for the formation of hydrogen peroxide with an elevated selectivity of hydrogen peroxide formation relative to the hydrogen used. Solutions of hydrogen peroxide in methanol obtainable by the process are suitable for use for the epoxidation of olefins.

18 Claims, No Drawings

PROCESS FOR THE PRODUCTION OF HYDROGEN PEROXIDE

CROSS REFERENCE TO RELATED APPLICATIONS

The present application claims the benefit of and priority to U.S. provisional application 60/670,229 filed on Apr. 12, 2005 and to German application 10 2005 016 877.9, filed on Apr. 13, 2005, both of which are hereby incorporated by reference in their entirety.

FIELD OF THE INVENTION

The invention is directed to a process for producing hydrogen peroxide by reacting hydrogen and oxygen in the presence of a noble metal catalyst in a liquid reaction medium, the reaction being performed in the presence of a sulfuric acid alkyl ester, and to solutions of hydrogen peroxide in methanol obtainable by this process and their use for the epoxidation of olefins.

BACKGROUND OF THE INVENTION

The production of hydrogen peroxide by direct synthesis from gas mixtures containing hydrogen and oxygen, by reacting the gas mixture in the presence of a liquid aqueous, aqueous-organic or organic reaction medium on a noble metal catalyst, is known. The hydrogen peroxide solutions obtainable by the direct synthesis process are of interest as oxidising agents for the catalytic oxidation of organic compounds.

In the direct synthesis of hydrogen peroxide, the undesired catalytic activity of the noble metal catalysts used in the catalytic breakdown of hydrogen peroxide to water and oxygen represents a problem. This undesired catalyst activity can be inhibited by adding a strong acid and a halide to the liquid reaction medium in an adequate concentration. However, the addition of acid and halide that is needed to obtain a high hydrogen peroxide selectivity makes the liquid reaction medium highly corrosive to metallic materials, in particular to stainless steel. Furthermore, if the hydrogen peroxide solution is used as an oxidising agent for the catalytic oxidation of organic compounds, the content of acid in particular leads to undesired secondary reactions and consecutive reactions.

One approach to solving the problem is the use of strongly acid catalyst supports, such as acid and superacid metal oxides, known from EP 504 741, activated carbon with sulfonic acid groups, known from EP 978 316, or ion-exchange resins with acid groups, known from EP 1 344 747. However, noble metal catalysts on strongly acid catalyst supports have the practical disadvantage that in the production of hydrogen peroxide the catalyst rapidly loses much of its catalytic activity.

There is therefore also a need for improved processes for the direct synthesis of hydrogen peroxide, which ensure a high selectivity of hydrogen peroxide formation with constantly high catalyst activity even without the addition of acid or with only low acid concentrations.

DESCRIPTION OF THE INVENTION

Surprisingly it has now been found that in the direct synthesis of hydrogen peroxide on a noble metal catalyst in the presence of a sulfuric acid catalyst a higher activity and selectivity of the catalyst for hydrogen peroxide formation can be obtained without the catalyst losing activity in the process. In the presence of a sulfuric acid alkyl ester a high selectivity of hydrogen peroxide formation can be achieved even with a reduced amount of acid or without the addition of acid.

The invention therefore provides a process for producing hydrogen peroxide by reacting hydrogen and oxygen in the presence of a noble metal catalyst in a liquid reaction medium, wherein the reaction is performed in the presence of a sulfuric acid alkyl ester.

The invention also provides a hydrogen peroxide solution obtainable by this process, comprising:
2 to 15 wt. % hydrogen peroxide,
0.5 to 20 wt. % water,
60 to 95 wt. % methanol,
$10^{-6}$ to $10^{-2}$ mol/l bromide and
$10^{-6}$ to 0.1 mol/l dimethyl sulfate and/or monomethyl sulfate.

The invention also provides a process for producing epoxides by reacting an olefin with hydrogen peroxide in the presence of a titanium-containing zeolite as catalyst using the hydrogen peroxide solution according to the invention.

In the process according to the invention for producing hydrogen peroxide, hydrogen and oxygen are reacted in the presence of a noble metal catalyst in a liquid reaction medium containing a sulfuric acid alkyl ester. Sulfuric acid alkyl esters within the meaning of the invention are the products of the esterification of sulfuric acid with an aliphatic alcohol. Both sulfuric acid dialkyl esters and sulfuric acid monoalkyl esters are suitable here, wherein sulfuric acid monoalkyl esters can also be used in the form of the alkali metal or ammonium salts. Sulfuric acid alkyl esters are preferably used in which the alkyl radical is selected from the group consisting of methyl, ethyl, n-propyl and n-butyl. Sulfuric acid alkyl esters having methyl as the alkyl radical are particularly preferred. Dimethyl sulfate, diethyl sulfate, sulfuric acid monomethyl ester, ammonium methyl sulfate, sodium methyl sulfate and potassium methyl sulfate are particular suitable for the process according to the invention.

The amount of sulfuric acid alkyl ester in the liquid reaction medium is chosen according to the other components of the liquid reaction medium such that an adequate activity and selectivity of the catalyst is achieved, and is preferably in the range from $10^{-6}$ mol/l to 0.1 mol/l and particularly preferably in the range from 0.001 mol/l to 0.1 mol/l. If the concentration of sulfuric acid alkyl ester is below the preferred range, then the addition of a strong acid is generally necessary to achieve an adequate selectivity, whereas in the presence of a sulfuric acid alkyl ester in the preferred concentration range the process can also be performed without the addition of a strong acid.

The liquid reaction medium can be an aqueous, aqueous-organic or organic reaction medium. If an aqueous-organic or organic reaction medium is used, an alcoholic solvent is preferably used as the organic component, primary alcohols being particularly preferred. A solvent from the series consisting of methanol, ethanol, n-propanol and n-butanol is preferably used, and particularly preferably methanol.

Regarding a use of the hydrogen peroxide solution as an oxidising agent for the oxidation of organic compounds, it is convenient if the water content in the reaction medium is kept as low as possible. The water content in the reaction medium is conveniently limited to a maximum of 20 wt. %, preferably 10 wt. %. Methanol with a water content of 2 to 10 wt. % is particularly preferably used as the solvent.

The liquid reaction medium used for the direct synthesis preferably also contains a halide in dissolved form in a quantity that is suitable to inhibit the breakdown of hydrogen peroxide on the noble metal catalyst during the direct synthesis. Bromide and/or iodide are used as halides, and preferably bromide. The liquid reaction medium contains the halide preferably in a concentration in the range from $10^{-6}$ to $10^{-2}$ mol/l, particularly preferably in the range from $10^{-5}$ to $10^{-3}$ mol/l and in particular in the range from $10^{-5}$ to $5\times10^{-4}$ mol/l. If the halide concentration is above the preferred range, then the stability of the hydrogen peroxide solution produced is compromised; if it is below the preferred range then an adequate hydrogen peroxide selectivity is generally no longer achieved. Lower halide concentrations are preferred in terms of the further use of the hydrogen peroxide solution formed. The halide can be added to the reaction medium in the form of an alkali metal or alkaline-earth metal salt, preferably as NaBr or NaI. The halide can likewise also be added in the form of the hydrohalic acid, for example as HBr or HI.

The liquid reaction medium used for the direct synthesis can optionally also additionally contain a strong acid. Strong acids within the meaning of the invention are all acids displaying a $pK_a$ value of less than 3 and preferably a $pK_a$ value of less than 2. Mineral acids such as sulfuric acid, phosphoric acid and nitric acid are particularly suitable. Sulfonic acids and phosphonic acids that are soluble in the medium can likewise be used. The acid concentration in the organic or organic-aqueous liquid medium is preferably in the range from 0.0001 to 0.5 mol/l and particularly preferably in the range from 0.001 to 0.1 mol/l. If the acid concentration is above the preferred range, then the liquid phase becomes undesirably corrosive; if it is below the preferred range then with low concentrations of sulfuric acid alkyl ester a reduction in hydrogen peroxide selectivity can occur. Lower acid concentrations are preferred in terms of the further use of the hydrogen peroxide solution formed.

The reaction is preferably performed with a gas mixture containing hydrogen and oxygen, the composition of which is chosen such that the gas mixture is not explosive. A gas mixture is preferably used which is reliably outside the explosive limit even taking into consideration the solvent partial pressure that is established. In addition to hydrogen and oxygen, the gas mixture conveniently also contains one or more inert gases, preferably nitrogen. The hydrogen content in the gas mixture is limited to a maximum of 6 vol. %, preferably a maximum of 5 vol. %. In particular the hydrogen content is in the range from 3 to 5 vol. %. The oxygen content in the gas mixture can be stoichiometric or hyperstoichiometric and is preferably in the range from 10 to 50 vol. %, in particular 15 to 45 vol. %. Hydrogen and oxygen are preferably supplied separately to the reactor. Oxygen can be supplied both in pure form and in the form of air or oxygen-enriched air. In a continuous reaction process the residual gas obtained at the reactor outlet can be wholly or partially returned to the reactor in order to reduce the cost of recovering unreacted hydrogen.

All catalysts known in the art for the direct synthesis of hydrogen peroxide and comprising one or more noble metals can be used for the process according to the invention. Particularly suitable catalysts are known from EP-A 1 038 833, page 3, line 10 to page 4, line 14, from U.S. Pat. No. 6,168,775, column 5, line 65 to column 6, line 64 and from WO 2005/009611, page 34, line 19 to page 42, line 20.

The catalytically active component of the catalyst comprises one or more noble metals in pure form or in the form of alloys. Preferred noble metals are the platinum metals, particularly palladium, and gold. Elements from the series consisting of Rh, Ru, Ir, Cu and Ag can also be present. Particularly preferred catalysts comprise as catalytically active metals at least 80 wt. % palladium and 0 to 20 wt. % platinum, and 0 to 20 wt. % gold and/or 0 to 5 wt. % silver in alloyed or unalloyed form.

The catalysts can be both support-free and support-bound, support-bound catalysts being preferred. The catalytically active noble metal(s) can be located on the surface of a support and/or can be arranged as particles in a uniform distribution within a bed of an inert support.

The supports are particulate materials such as powders, extrudates, granules, or other mouldings formed from a powdered material. Oxidic or siliceous supports are preferably used, particularly aluminium oxide, silica, titanium dioxide, zirconium dioxide and zeolites. Alternatively, carbon-based supports, such as activated carbon supports, can also be used.

It is possible to mix the catalytically active component present in very finely dispersed form with a powdered support, to plasticise and shape the mixture and to strengthen the mouldings by calcination. According to an alternative, it is also possible to impregnate a prefabricated, shaped support with a suspension containing the very finely dispersed catalytically active component, producing a so-called shell catalyst. When the catalytically active material is applied to or in the support, known binders, such as water glass, calcium oxalate, boric acid and other glass-forming compositions, can also be present. Application of the catalytically active material to a support is conventionally followed by a calcining step at 300 to 600° C. Finally the catalytically active supported catalysts can also be obtained by impregnating the support with a solution containing a compound of the catalytically active metals, with subsequent hydrogenating, calcining and washing steps.

The process according to the invention can be performed both continuously and batchwise, a continuous reaction process being preferred. The noble metal catalyst can be used here in any form, particularly in the form of a suspension or in the form of a fixed bed.

The noble metal catalyst is preferably used in the form of a fixed bed. The size of the particles in the fixed bed can lie within broad ranges, in particular in the range from 0.1 to 10 mm. If mixtures of catalytically active and inactive particles are used, catalytically active particles having a size in the range from 0.02 to 0.1 mm can also be used. A small particle size leads to a greater pressure drop, whilst with too large a particle size the catalytically active surface area is reduced. Particle sizes in the range from 0.1 to 5 mm, in particular 0.1 to 2 mm and particularly preferably 0.1 to 0.5 mm, lead to high productivities.

In a preferred embodiment of the process according to the invention a reactor is used which comprises one or more fixed beds with the noble metal catalyst. The reactor is flooded with the liquid reaction medium and the gas mixture is distributed in the form of gas bubbles in the reaction medium contained in the reactor. The reactor is designed and operated in such a way that no gas cushions are formed in the reactor in which the gas mixture is permanently in contact with the reactor wall or with metal reactor fittings. An example of such an embodiment according to the invention is the performance of the reaction in a bubble column, wherein the liquid reaction medium and the gas mixture are introduced in the lower part of the bubble column and the hydrogen peroxide solution that is produced is removed together with unreacted gas from the top of the bubble column reactor. The bubble column reactor comprises a fixed bed of support-bound catalyst particles or a mixture of catalyst-containing and catalyst-free particles, wherein the fittings which hold the fixed catalyst bed in the reactor are designed in such a way that at no point is a gas cushion formed which is permanently in contact with the reactor wall or with metal fittings. Permanently in contact means here that the surface is not wetted with the liquid reaction medium over an extended period but is in direct contact with the gas phase. The surface preferably remains unwetted by the liquid medium for no longer than 30 minutes at any point in the reactor, in particular for no longer than 30 seconds. In the most preferred embodiment the liquid reaction medium is passed through the reactor in such a way that the surface of the reactor is constantly wetted by the liquid reaction medium at every point.

If a fixed-bed catalyst is used, the liquid reaction medium is preferably fed to the reactor at a rate that leads to a cross-sectional load on the catalyst from the liquid phase in the range from 0.3 to 200 m/h, relative to the empty cross-section of the reactor. The cross-sectional load is preferably in the range from 0.3 to 20 m/h and particularly preferably in the range from 1 to 10 m/h. In the preferred range of cross-sectional load, hydrogen peroxide solutions can be produced with a hydrogen peroxide content of 4 to 12 wt. %, a high hydrogen peroxide selectivity, a high space-time yield and a high catalyst lifetime being achieved at the same time.

The reaction conditions in the process according to the invention in terms of pressure and temperature correspond to those known in the art. Thus the reaction temperature is generally in the range from 0 to 90° C., a temperature range from 20 to 50° C. being preferred. The pressure is generally in the range of atmospheric pressure or a slightly reduced pressure to around 10 MPa. The reaction is preferably performed at a pressure in the range from 0.5 to 5 MPa.

In the presence of sulfuric acid alkyl esters the noble metal catalyst exhibits a high and lasting activity for the formation of hydrogen peroxide with an elevated selectivity of hydrogen peroxide formation relative to the hydrogen used, even if gas mixtures containing hydrogen and oxygen are used which have a composition outside the explosive range. Reaction media can be used here which have lower contents of halides such as bromide and/or iodide and of strong acids than is the case in the absence of sulfuric acid alkyl esters.

The process according to the invention can be particularly advantageously integrated into an overall process for the oxidation of an organic substrate with hydrogen peroxide, since hydrogen peroxide solutions produced with the process according to the invention contain lower amounts of components which can lead to undesired secondary reactions and consecutive reactions in a subsequent oxidation reaction. Particularly advantageous here are solutions of hydrogen peroxide in methanol produced by the process according to the invention which comprise 2 to 15 wt. % and preferably 5 to 12 wt. % of hydrogen peroxide, 0.5 to 20 wt. % and preferably 2 to 10 wt. % of water, 60 to 95 wt. % of methanol, $10^{-6}$ to $10^{-2}$ mol/l and preferably $10^{-5}$ to $10^{-3}$ mol/l of bromide, and $10^{-6}$ mol/l to 0.1 mol/l and preferably 0.001 mol/l to 0.1 mol/l of dimethyl sulfate and/or monomethyl sulfate. The solutions can additionally also contain up to 0.1 mol/l of a strong acid, preferably sulfuric acid.

The solutions according to the invention of hydrogen peroxide in methanol are particularly suitable for the epoxidation of olefins, preferably of propene, with hydrogen peroxide in the presence of a titanium-containing zeolite as catalyst. The solutions according to the invention of hydrogen peroxide in methanol can be used here in the reaction with no further treatment or additives and in comparison to solutions of hydrogen peroxide in methanol produced by direct synthesis according to the prior art they give rise to an improved selectivity of epoxide formation and fewer byproducts due to ring-opening reactions. If solutions are used which additionally contain a strong acid, the content of strong acid is advantageously wholly or partially neutralised by the addition of a base, preferably ammonia, before being used for epoxidation. The epoxidation can be performed under the reaction conditions known from the prior art, for example from EP-A 0 100 119, and with the known titanium-containing zeolite catalysts. The epoxidation is preferably performed under the reaction conditions described in WO 02/085873 on page 6, line 17 to page 11, line 26, the solution according to the invention of hydrogen peroxide in methanol being used in place of the aqueous hydrogen peroxide solutions used in WO 02/085873.

The invention is illustrated by the examples and comparative examples below.

EXAMPLES

Example 1

The direct synthesis was performed in a bubble column reactor with an internal diameter of 16 mm and a length of 40 cm. The reactor comprises a fixed catalyst bed with a bed volume of approximately 80 ml. A mixture of catalytically active metal particles and inert particles was used as the catalyst. Catalytically active particles consisting of 95% Pd and 5% Au were produced by analogy to DE 199 12 733. Granular alpha-aluminium oxide from Ceramtech AG with the name "Stemalox-Sprühkorn, gebrannt 0-0.5 mm $Al_2O_3$-Gehalt 85%" (Stemalox spray particles, calcined, 0-0.5 mm, $Al_2O_3$ content 85%) was used as the inert material. Before being used, the granules were freed from the <0.1 mm fraction by screening. The very fine particle metal catalyst powder was mixed with the oxidic support powder. The Pd content of the mixture of catalyst particles and inert particles was 0.25 wt. %.

The reactor was operated as a flooded bubble column reactor with a cocurrent flow of gas and liquid at a pressure of 5 MPa (50 bar) and a reaction temperature of 25° C. A mixture of 98 parts by weight of methanol and 2 parts by weight of water with 0.0001 mol/l of sodium bromide, 0.01 mol/l of sulfuric acid and 0.01 mol/l of dimethyl sulfate was used as the liquid reaction medium. The liquid reaction medium was supplied to the bottom of the reactor at a rate of 120 ml/h. The flow rate of the liquid and the reactor cross-section gave rise to a liquid cross-section load of 0.6 m/h. At the same time 230 Nl/h of a gas mixture consisting of 3 vol. % of hydrogen, 20 vol. % of oxygen and 77 vol. % of nitrogen were introduced at the bottom of the reactor. The hydrogen peroxide solution that was formed was removed together with unreacted gas at the top of the reactor in such a way that no gas cushion formed inside the reactor.

After operating the reactor for 24 hours the hydrogen conversion was 49% and the hydrogen peroxide solution that was removed contained 3.8 wt. % of hydrogen peroxide. The selectivity of hydrogen peroxide formation was 71%, relative to unreacted hydrogen. The catalyst activity was 10.6 g $H_2O_2$/g Pd * h.

Example 2

Not According to the Invention

Example 1 was repeated, but no dimethyl sulfate was added to the reaction medium. After operating the reactor for 24 hours the hydrogen conversion was 45% and the hydrogen peroxide solution that was removed contained 3.12 wt. % of hydrogen peroxide. The selectivity of hydrogen peroxide formation was 64%, relative to unreacted hydrogen. The catalyst activity was 8.5 g $H_2O_2$/g Pd * h.

Example 3

Not According To the Invention

Example 2 was repeated, but the concentration of sulfuric acid was reduced to 0.001 mol/l.

After operating the reactor for 24 hours the hydrogen conversion was 45% and the hydrogen peroxide solution that was removed contained 2.25 wt. % of hydrogen peroxide. The selectivity of hydrogen peroxide formation was 46%, relative to unreacted hydrogen. The catalyst activity was 6.1 g $H_2O_2$/g Pd * h.

Example 4

Example 1 was repeated, but no sulfuric acid was added to the reaction medium and the concentration of dimethyl sulfate was increased to 0.02 mol/l.

After operating the reactor for 24 hours the hydrogen conversion was 49% and the hydrogen peroxide solution that was removed contained 4.0 wt. % of hydrogen peroxide. The selectivity of hydrogen peroxide formation was 74%, relative to unreacted hydrogen. The catalyst activity was 11.0 g $H_2O_2$/g Pd * h. The catalyst activity and selectivity of hydrogen peroxide formation were unchanged even after 72 hours of reactor operation.

CONCLUSIONS

A comparison of Examples 1 and 2 shows that in the presence of dimethyl sulfate a higher activity and selectivity of the catalyst for the formation of hydrogen peroxide was achieved than in otherwise identical conditions without the addition of dimethyl sulfate.

Example 3 shows in comparison to Example 2 that in the absence of a sulfuric acid alkyl ester the selectivity of hydrogen peroxide formation falls sharply with a reduced acid concentration. Example 4 shows, by contrast, that in the presence of dimethyl sulfate, even without the addition of a strong acid, a high selectivity of hydrogen peroxide formation was achieved.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A process for producing hydrogen peroxide by reacting hydrogen and oxygen in the presence of a noble metal catalyst in a liquid reaction medium, wherein the reaction is performed in the presence of a sulfuric acid alkyl ester.

2. The process of claim 1, wherein the sulfuric acid alkyl ester is a sulfuric acid dialkyl ester, a sulfuric acid monoalkyl ester or an alkali metal or ammonium salt of a sulfuric acid monoalkyl ester.

3. The process of claim 2, wherein the alkyl radical in the sulfuric acid alkyl ester is chosen from the group consisting of: methyl; ethyl; n-propyl; and n-butyl.

4. The process of claim 2, wherein the alkyl radical in the sulfuric acid alkyl ester is methyl.

5. The process of claim 1, wherein the reaction is performed in an aqueous, aqueous-organic or organic reaction medium containing a bromide and/or iodide in dissolved form.

6. The process of claim 5, wherein the aqueous-organic or organic reaction medium comprises a solvent selected from the group consisting of: methanol; ethanol; n-propanol and n-butanol.

7. The process of claim 5, wherein the aqueous-organic or organic reaction medium comprises methanol.

8. The process of claim 5, wherein the sulfuric acid alkyl ester is a sulfuric acid dialkyl ester, a sulfuric acid monoalkyl ester or an alkali metal or ammonium salt of a sulfuric acid monoalkyl ester.

9. The process of claim 8, wherein the alkyl radical in the sulfuric acid alkyl ester is chosen from the group consisting of: methyl; ethyl; n-propyl; and n-butyl.

10. The process of claim 8, wherein the alkyl radical in the sulfuric acid alkyl ester is methyl.

11. The process of claim 1, wherein the reaction is performed with a non-explosive gas mixture containing hydrogen and oxygen.

12. The process of claim 1, wherein the noble metal catalyst comprises metallic palladium on a support.

13. The process of claim 12, wherein the sulfuric acid alkyl ester is a sulfuric acid dialkyl ester, a sulfuric acid monoalkyl ester or an alkali metal or ammonium salt of a sulfuric acid monoalkyl ester.

14. The process of claim 13, wherein the alkyl radical in the sulfuric acid alkyl ester is chosen from the group consisting of: methyl; ethyl; n-propyl; and n-butyl.

15. The process of claim 13, wherein the alkyl radical in the sulfuric acid alkyl ester is methyl.

16. The process of claim 1, wherein the reaction is performed in a reactor in which the noble metal catalyst is arranged in the form of one or more fixed beds and a gas mixture containing hydrogen and oxygen is passed through the reactor in such a way that, at no point, is the surface of the reactor permanently in contact with the gas mixture being passed through the reactor.

17. The process of claim 16, wherein:
   a) the reaction is performed with a non-explosive gas mixture containing hydrogen and oxygen;
   b) the noble metal catalyst comprises metallic palladium on a support;
   c) the sulfuric acid alkyl ester is a sulfuric acid dialkyl ester, a sulfuric acid monoalkyl ester or an alkali metal or ammonium salt of a sulfuric acid monoalkyl ester.

18. The process of claim 17, wherein the alkyl radical in the sulfuric acid alkyl ester is chosen from the group consisting of: methyl; ethyl; n-propyl; and n-butyl.

* * * * *